US00PP10393P

United States Patent [19]

Plate

[11] Patent Number: Plant 10,393

[45] Date of Patent: May 12, 1998

[54] DORITAENOPSIS ORCHID PLANT NAMED 'APOSYA'

[75] Inventor: Renate Plate, Bremen, Germany

[73] Assignee: Wolfgang Bock Pflanzenexport KG, Bremen, Germany

[21] Appl. No.: 744,351

[22] Filed: Nov. 4, 1996

[51] Int. Cl.[6] ..... A01H 5/00

[52] U.S. Cl. ..... Plt./87.3

[58] Field of Search ..... Plt./87.3

*Primary Examiner*—James R. Feyrer

*Assistant Examiner*—Elizabeth C. Kemmerer

*Attorney, Agent, or Firm*—Foley & Lardner

[57] ABSTRACT

A new and distinct *Doritaenopsis* orchid variety named 'Aposya' particularly characterized by its magenta flowers. Its horticultural traits further include economical ropagation via tissue culture, very rapid growth, and plant dimensions suitable for package and shipping to market.

2 Drawing Sheets

The present invention comprises a new and distinct cultivar of *Doritaenopsis*, a bigeneric hybrid of *Doritis*× *Phalaenopsis* of the family Orchidaceae, referred to by the cultivar name 'Aposya'. The new cultivar is a hybrid selected from the progeny of a cross of parent plants identified below.

*Doritaenopsis* comprise a group of bigeneric hybrids generally intermediate in character between the parent genera, which are suitable for cultivation in the home or greenhouse. The parent genera of *Doritaenopsis* are predominantly epiphytic or rock-dwelling, and are native to tropical Asia, Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

*Doritaenopsis* orchids, often referred to as 'Moth Orchids' in the horticultural trade, are frequently used to furnish cut flowers for the florist trade, or sold as flowering potted plants for home or interiorscape.

*Doritaenopsis* produce upright racemes, often with many showy flowers which open in succession beginning with the lowermost. The flowers possess three sepals, and three petals, the lateral ones being alike. The lowermost petal, called the labellum, is three lobed and is often more brightly colored than the other flower segments. Flower colors are frequently various shades of pink.

*Doritaenopsis* orchids are typically propagated from seeds. However, Doritaenopsis is capable of being asexually reproduced from off-shoots which frequently arise from the lower bracts of the inflorescence. The resulting plants are detached from the mother plant and may be planted in a suitable substrate. Asexual propagation of *Doritaenopsis* can also be performed by tissue culture, although this technique is not widely practiced commercially because it is often relatively inefficient and costly as currently applied.

The new cultivar named 'Aposya' is a product of a breeding program carried out by the inventor Renate Plate in Bremen, Germany. The new cultivar is a result of a cross of selected, but unnamed parentage made by the inventor in Bremen, Germany in 1984. The new cultivar was discovered from the progeny of the stated cross in Bremen, Germany by the inventor in September 1986. Asexual propagation by tissue culture done under the supervision of the inventor in Bremen, Germany was used to increase the number of plants for evaluation and has demonstrated the stability of the combination of characteristics from generation to generation.

The following observations, measurements and values describe plants grown in Lake Worth, Fla. under greenhouse conditions which closely approximate those generally used in horticultural practice.

The following traits have been repeatedly observed to be characteristics which in combination distinguish 'Aposya' from generally available seedling-derived *Doritaenopsis* common in commercial cultivation.

1. The flowers produced by 'Aposya' are brilliant magenta with yellow markings in the center.

2. The inflorescence produced by 'Aposya' is tall, straight and sturdy with closely spaced flowers. It is easily staked and packaged for shipping.

3. Plants of 'Aposya' grow very quickly, producing marketable flowering plants in approximately 9–11 months.

4. 'Aposya' blooms during the summer, unlike most *Phalaenopsis* hybrids which bloom during the winter.

5. Plants of 'Aposya' may be propagated economically and uniformly using tissue culture.

It is difficult to compare the new cultivar with commercially available seedling-derived *Doritaenopsis* which are heterogeneous genetically, and typically lack uniformity in growth vigor, habit, and flower quality. Because of these inconsistent characteristics, a direct comparison for 'Aposya' is not possible. 'Aposya' is a single genotype asexually propagated via tissue culture, and its combined horticultural properties listed above are uniform and predictable.

All color references are measured against The Royal Horticultural Society color chart. Colors are approximate as color depends on horticultural practices such as light level and fertilization rate, among others, without, however any change in genotype.

In the color photographic drawings, the photograph on Sheet 1 comprises a top perspective view of the inflorescence and foliage of a group of plants of 'Aposya' in 10.2 cm pots. The photograph was taken approximately 16 months after planting 16 week old liners obtained by tissue culture and grown under appropriate growing conditions.

The photograph on Sheet 2 is a close up view of the flowers.

Colors are as accurate as possible with color illustration of this type.

Orgin: Seedling from a cross of selected, but unnamed parentage.

Classification: *Doritaenopsis hybrid*, cv. 'Aposya'.

Propagation: Asexual propagation by tissue culture.

Inflorescence:

*Flower description.*—The sepals and petals are brilliant magenta. The reverse side of the sepals and petals is somewhat lighter in color. The sepals are elliptic-ovate in shape, the lateral petals are broadly ovate. The sepals and petals are flat or slightly cupped. The lower sepals and labellum are fused at their base. The labellum has three lobes and callosity at the central junction of the lateral lobes and base of the midlobe. The lateral lobes of the labellu fold upward toward the column, the midlobe extends forward. The lateral lobes of the labellum are narrow and rectangular in shape. The midlobe is triangular to cruciform in shape with bluntly rounded apices. The labellum is a dark magenta with a yellow center, the callosity is yellow.

*Dimension.*—Overall: Approximately 4.3 cm to 5.0 cm wide, and 4.1 cm to 3.8 cm in height. Sepals: Approximately 2.2 cm to 2.4 cm long, and 1.4 cm to 1.6 cm wide. Petals: Approximately 2.2 cm to 2.5 cm long, and 1.6 cm to 1.8 cm wide. Labellum: Approximately 1.8 cm to 2.1 cm long, and 1.3 cm wide (not flattened).

*Flower color.*—Sepals: Adaxial surface: 81 A-B. Abaxial surface: 82 B. Lateral Petals: Adaxial surface: 81 B. Abaxial surface: 82 B. Labellum: Adaxial surface: Lateral lobes: 13 A-B tipped with 60 A. Midlobe: 82 A becoming 60 A on lateral apices. Callosity: 21 A. Abaxial surface: Lateral lobes: 13 A-B tipped with 60 A. Midlobe: 82 B tinged with 60 A on lateral apices. Raceme: Dimension: The raceme is typically staked upright. The raceme is approximately 70 cm from base to tip, and 0.40 cm in diameter at its midpoint. The raceme is 200 C, 147 A in color.

*Flowering time.*—For untreated plants as depicted in the photograph on Sheet 1 and which are flowering for the second time, 8–20 flowers/unopened buds are present. First flowers can be expected approximately 4–6 months after planting a 16 week old liner; approximately 8–10 flowers are present.

Reproductive organs: The stamens, style and stigmas are fused into a single short column, possessing one terminal anther with pollen grains united into a pollinia, which are covered by an anther cap. The stigma is located under the column behind the pollinia. Ovary inferior, three carples present.

*Column.*—The column is approximately 8 mm long, 5 mm wide, and is darker than but closest to 82 A in color.

*Pollinia.*—Two 1.0 mm rounded masses of pollen present, 24 A in color. Viscidium present.

*Stigma.*—Concave, round 4 mm–5 mm area under column, 147C-D in color.

*Ovary.*—11 mm long, 2.0 mm diameter, color 84 A. Pedicel approximately 1.8 cm to 2.0 cm long, 2.0 mm diameter, and 147 B-C in color.

General appearance: Under appropriate growing conditions, plants of 'Aposya' (excluding raceme) attain a mature size of approximately 14.0 cm to 17.5 cm in height and approximately 35 cm in width.

*Leaves.*—Form: The leaf blade is long and elliptic with obtuse to slightly retuse apex and a cuneate base. The margins are entire. The midrib is straight over the length of the leaf. The leaf blade is folded upward from the midrib. The upper leaf surface is dull or slightly glossy on newly emerged leaves. The leaves are leathery, and thick. Size: Leaf blades of a mature sized plant are approximately 18.4 cm to 22.5 cm in length and approximatly 5.4 cm to 6.7 cm in width measured at the widest point. Veins: Veins are sunken, within the thick leaf blade. Color: Adaxial surface: Darker and greener than, but closest to 137 A. Abaxial surface: Darker than, but closest to 147 B, with streaks and speckles of anthiocyanous 187 A throughout.

*Roots.*—Very thick greenish white fleshy roots.

GENERAL OBSERVATIONS

*Doritaenopsis* 'Aposya' produces flowers which are brilliant magenta with yellow markings in the center. The inflorescence is tall, straight and sturdy with closely spaced flowers. It is easily packaged for shipping. The plant grows very quickly to marketable size. 'Aposya' can be economically propagated via tissue culture.

I claim:

1. A new and distinct cultivar of *Doritaenopsis* Orchid plant named 'Aposya', as illustrated and described.

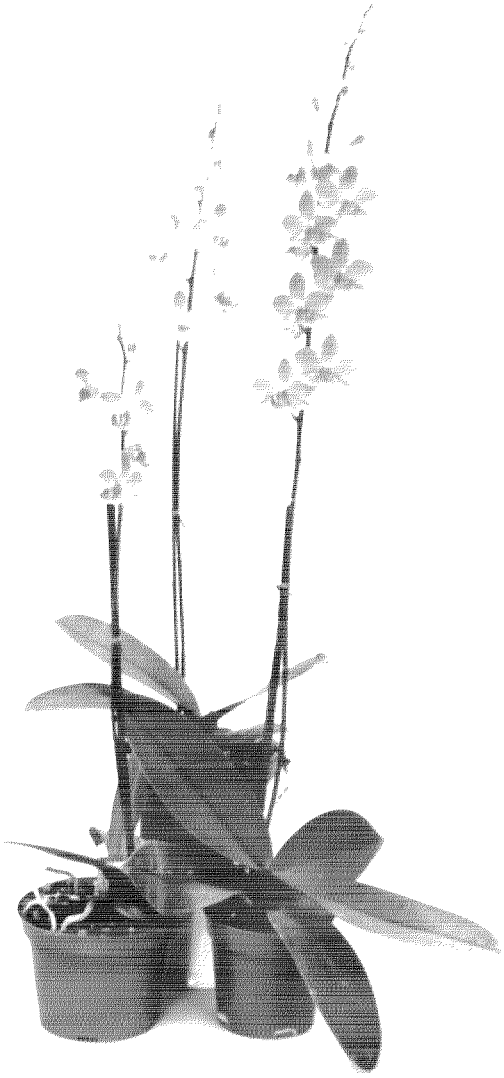

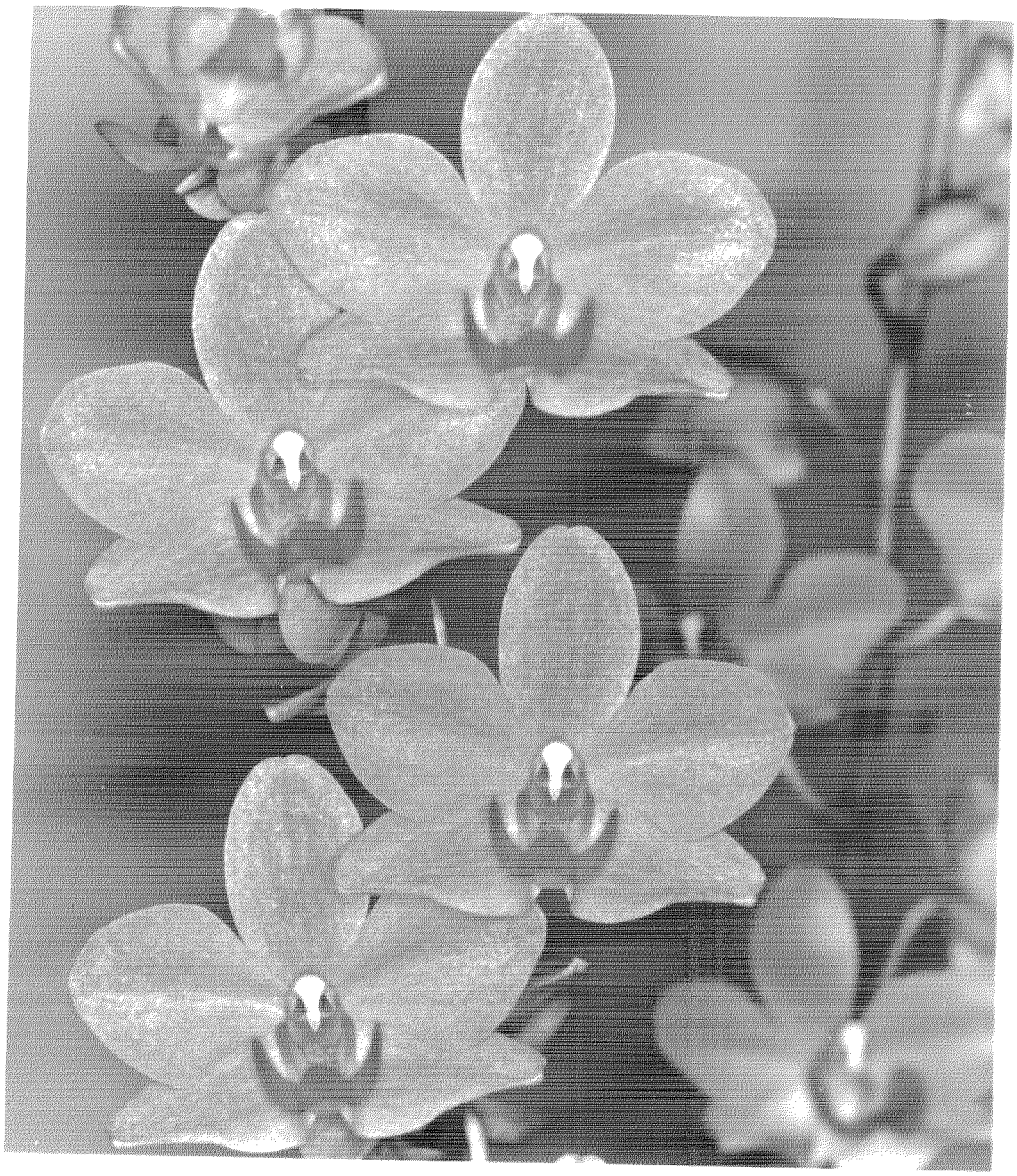

* * * * *